US00PP28325P3

(12) United States Plant Patent
Suphachadiwong

(10) Patent No.: US PP28,325 P3
(45) Date of Patent: Aug. 22, 2017

(54) ***VANDA* PLANT NAMED 'SPCDW1404'**

(50) Latin Name: ***Vanda* spp. Jones ex R. Br.**
Varietal Denomination: SPCDW1404

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Bangphra (TH)

( * ) Notice: Subject to any disclaimer, the term of this patent is extended or adjusted under 35 U.S.C. 154(b) by 61 days.

(21) Appl. No.: 14/757,055

(22) Filed: Nov. 13, 2015

(65) Prior Publication Data

US 2016/0143202 P1 May 19, 2016

(30) Foreign Application Priority Data

Nov. 14, 2014 (QZ) ..... 2014/2941

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

Phillo Flowers blog A visit to Anco—the *Vanda* Orchid nursery 2012 retrieved on Mar. 1, 2017, retrieved from the Internet at <http://www.philloflowers.com/blog/vanda-orchid-nursery/> 10 pp.*

* cited by examiner

*Primary Examiner* — June Hwu
(74) *Attorney, Agent, or Firm* — Samuel R. McCoy, Jr.

(57) ABSTRACT

A new and distinct *Vanda* cultivar named 'SPCDW1404' which is characterized by the combination of a dark purple general tonality of the flower with a pronounced deep purple spotting pattern of both the sepals and petals, with undulating margins of both the sepals and petals, as well as the stability of all characteristics from generation to generation. The new variety is a *Vanda*, typically produced as an indoor ornamental plant.

3 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1404'.

CROSS REFERENCE TO RELATED APPLICATIONS

This application claims priority to the Community Plant Variety Rights application number 2014/2941, filed Nov. 14, 2014, which is herein incorporated by reference.

BACKGROUND OF THE INVENTION

Parentage: The *Vanda* variety 'SPCDW1404' is the result of a planned breeding program. The new variety originated as a seedling from the crossing of the unpatented, proprietary seed parent *Vanda* 'RCB' with the unpatented, proprietary pollen parent referred to as *Vanda* 'D2N'. Both parents were developed by, and are owned by, the inventor and were never commercially released. The crossing was made by the inventor in his research greenhouse in Bangphra, Thailand in October of 2002.

The new variety was first selected in June of 2008, in a research greenhouse in Bangphra, Thailand belonging to the inventor. After identifying the new variety as a potentially interesting selection, the inventor continued confidential testing and propagation of 'SPCDW1404', assessing stability of the unique characteristics of this variety.

Asexual Reproduction: Asexual reproduction of the new cultivar 'SPCDW1404', by way of mericloning, was first initiated in April of 2009 at a commercial laboratory belonging to the inventor in Bangphra, Thailand, with the first mericlones so reproduced flowering in 2014. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1404' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1404'. These characteristics in combination distinguish 'SPCDW1404' as a new and distinct *Vanda* cultivar:

1. *Vanda* 'SPCDW1404' exhibits a unique dark purple general tonality of the sepals and petals; and 2. *Vanda* 'SPCDW1404' exhibits a pronounced deep purple spotting pattern of the sepals and petals; and
3. *Vanda* 'SPCDW1404' exhibits pronounced undulation of the sepal and petal margins.

BOTANICAL DESCRIPTION OF THE PLANT

Figure 1:
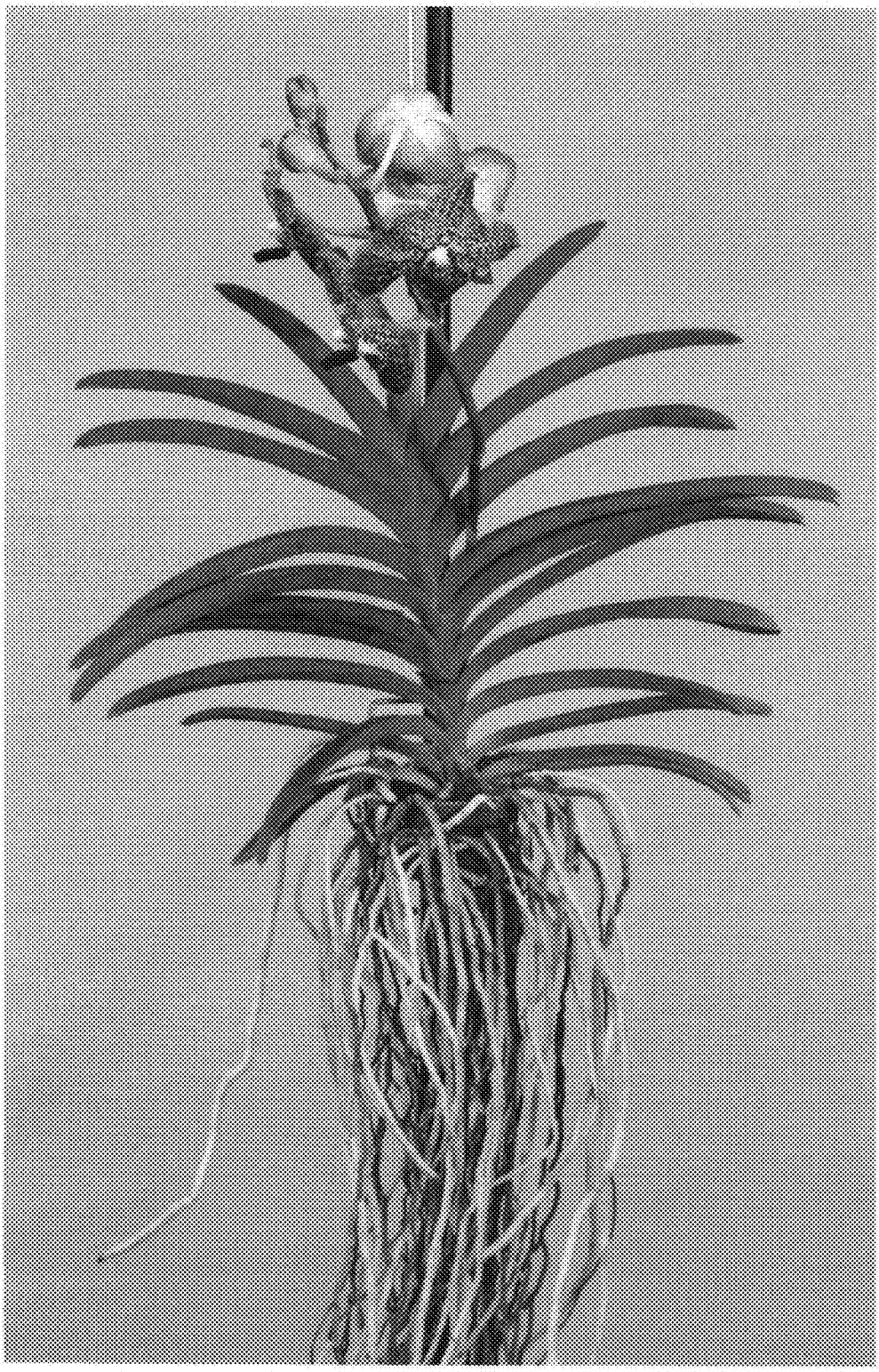
FIG. 1 illustrates, as nearly true as it is reasonably possible to make the same in color photographs of this type, an exemplary plant of 'SPCDW1404' grown in a commercial greenhouse in Honselersdijk, the Netherlands. This plant is approximately 5 years old from the time of mericloning, shown planted in an 8 by 8 cm container.
Figure 2:
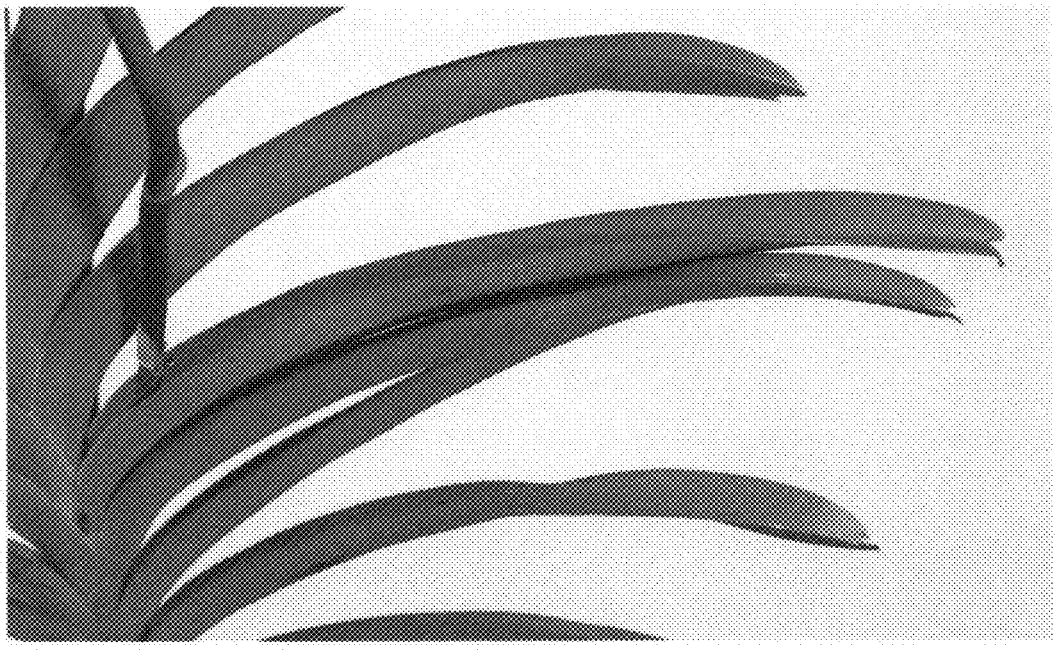
FIG. 2 illustrates, as nearly true as it is reasonably possible to make the same in color photographs of this type, the typical foliage of 'SPCDW1404'.
Figure 3:
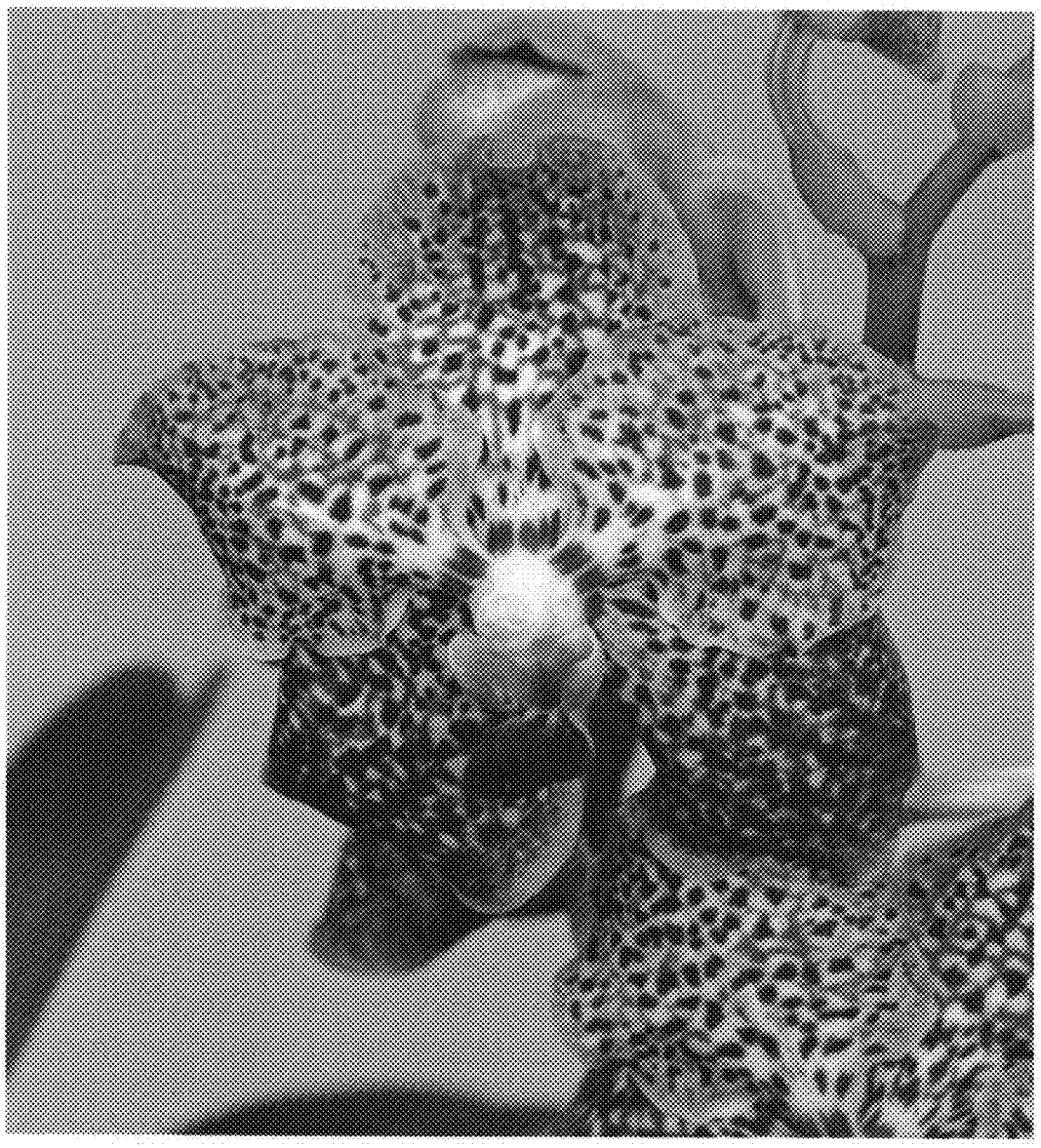
FIG. 3 illustrates, as nearly true as it is reasonably possible to make the same in color photographs of this type, the typical flowers of 'SPCDW1404'.

The following observations and measurements made in October of 2015 describe averages from a sample set of six specimens of five year-old 'SPCDW1404' plants grown in a greenhouse in Honselersdijk, the Netherlands. Temperatures ranged were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1404' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'SPCDW1404' and comparisons with other varieties of *Vanda* are provided below.

Plant description:

*Growth habit*.—Perennial; monopodial, upright. Single monopodial leafy stem, with flowers carried slightly above the leaf plane, inflorescences grow from the leaf axils.

*Average height from base (plant grown in hanging basket, so no soil line present) to top of foliage*.—37.5 cm.

*Average height from base (plant grown in hanging basket, so no soil line present) to top of flowers*.—45.4 cm.

*Plant spread*.—Average of 46.5 cm.

*Normal pot size*.—Hanging basket (8 by 8 cm, square).

*Growth rate*.—Moderate.

*Plant vigor*.—Moderate.

*Propagation type*.—Propagation Type — Meristematic tissue culture propagation using the base of the leaves.

*Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility*.—Similar to other *Vanda* varieties.

*Environmental tolerances*.—Adapt to, at least, USDA Zones 11 and 12; high tolerance to rain; moderate to high tolerance to wind.

Root system:

*General*.—Densely rooting; with aerial roots only.

*Dimensions, mature roots*.—56.1 cm long with a diameter of 0.5 cm, on average.

*Texture*.—Fleshy; non-fibrous.

*Color*.—Greyed-Green, near RHS 192C to 192D; root apex is yellow-green, RHS 146A.

Stem:

*Branching habit*.—Single monopodial leafy stem.

*Number of primary (main) stems per plant*.—One.

*Number of secondary (lateral) branches per plant*.—None.

*Appearance and shape*.—Circular, formed by the leaf sheaths.

*Length*.—22.5 cm.

*Diameter*.—0.9 cm.

*Internode length*.—0.5 cm.

*Luster*.—Matte.

*Aspect*.—Near vertical.

*Strength*.—Very strong.

*Color, juvenile*.—Yellow-green, near 150D.

*Color, mature*.—Yellow-green, near 150D.

*Color at internodes*.—Yellow-green, near 150D.

*Pubescence*.—Glabrous.

Foliage:

*Arrangement*.—Distichous.

*Quantity*.—Approximately 23 leaves per plant.

*Dimensions*.—23.0 cm long and 2.5 cm wide, on average.

*Shape of blade*.—Ligulate; strongly carinate.

*Aspect*.—Moderately curved.

*Apex*.—Unequal praemorse.

*Base*.—Sheathing.

*Sheath dimensions*.—2.7 cm long and 1.5 cm wide, on average.

*Sheath color*.—Yellow-Green, near RHS 145C to 145D.

*Margin*.—Entire.

*Pubescence, texture and luster of adaxial surface*.—Glabrous, smooth, and very slightly glossy.

*Pubescence, texture and luster of abaxial surface*.—Glabrous, smooth, and matte.

*Color*.—Juvenile foliage, adaxial surface — Green, near RHS 143A; darker toward the margins, near 137B. Juvenile foliage, abaxial surface — Green, near RHS 143A to 143B. Mature foliage, adaxial surface — Green, nearest to RHS 137B. Mature foliage, abaxial surface — Yellow-green RHS 144A.

*Venation*.—Parallel.

*Venation color, adaxial surface*.—Green, near RHS 137B.

*Venation color, abaxial surface*.—Yellow-green RHS 144A.

*Petiole*.—No petioles present, leaves sessile.

Inflorescence:

*Inflorescence arrangement*.—Axially placed raceme.

*Natural flowering season*.—Autumn into winter.

*Inflorescence quantity*.—One.

*Flowers per inflorescence*.—Average of 7 open flowers and 1 unopened flower bud.

*Inflorescence height*.—Approximately 18.5 cm (measured from base of lowest flower to top of upper flower).

*Inflorescence width*.—Approximately 17.4 cm.

*Peduncle*.—Dimensions — Approximately 32.0 cm long and 0.6 cm wide. Aspect — Approximately 30° angle to lateral branch axis. Strength — Moderately strong. Texture and luster — Glabrous and moderately glossy. Color — Green, near RHS 143B.

Bud:

*Length*.—Average of 1.9 cm.

*Diameter*.—Average of 1.8 cm.

*Shape*.—Broad obovate.

*Pubescence, texture and luster*.—Glabrous, smooth and moderately glossy.

*Color*.—Yellow-green, near RHS 145B; apex tinged with purple, near N77C.

Flower:

*Flower type*.—Zygomorphic (orchidaceous), typical shape for the genus *Vanda*.

*Flowering habit*.—Moderate.

*Shape*.—Zygomorphic, single; consisting of three sepals and three petals, one of which is transformed into a labellum; the two lateral petals heavily overlap the dorsal sepal and the lateral sepals; dorsal sepal and lateral sepals are free.

*Aspect*.—Flowers are outward-facing to slightly nodding.

*Height*.—Approximately 10.6 cm.

*Diameter*.—Approximately 10.0 cm.

*Depth*.—Approximately 4.6 cm.

*Fragrance*.—No fragrance.

*Lastingness*.—3 weeks.

*Persistent*.—Self-cleaning.

*Petals*.—Quantity of Petals — 3; two conventional petals and one labellum. Arrangement — One lateral petal on each side. Length — Approximately 4.9 cm. Width — Approximately 4.6 cm. Shape — Broad ovate to near orbicular. Apex — Obtuse. Base — Cuneate. Margin — Entire; moderately undulate. Pubescence, texture and luster of upper surface — Glabrous, velvety and matte. Pubescence, texture and luster of lower surface — Glabrous, velvety and matte. Color when opening, upper surface — Green-white, near RHS 157C to 157D; tinged greyed-purple at and near the apex, near RHS N187D; petal moderately dotted with greyed-purple at the apex, near RHS N187A; striped with violet at the base, nearest to RHS 86D. Color when opening, lower surface — Green-white, near RHS 157D; tinged with violet-blue, near RHS 90D and lighter, at and near the apex; petal slightly dotted with greyed-purple, RHS N187A to N187B. Color when fully opened, upper surface — White, near RHS 155C; tinged with violet, near RHS N88C to N88D, at and near the apex; petal densely dotted with violet RHS 83A. Color when fully opened, lower surface — White, near RHS 155C; tinged with violet-blue, near RHS 90D, at and near the apex. Fading, upper surface — Not fading. Fading, lower surface — Not fading. Venation color, fully opened, upper surface — Violet, near N87A to N87C. Venation color, fully opened, lower surface — Violet-blue, near 90D and lighter.

*Labellum*.—Shape — Three-lobed; the shape of the lateral lobes is broad ovate and the aspect is heavily involute; the central lobe is ovate to near rhombic and the aspect is heavily revolute. Length — Central lobe — Approximately 2.1 cm. Lateral lobes — Approximately 1.0 cm. Width — Central lobe — Approximately 1.0 cm. Lateral lobes — Approximately 0.6 cm. Apex — Central lobe — Emarginate. Lateral lobes — Obtuse. Base — Central lobe — Cuneate. Lateral lobes — Cuneate. Margin — Entire; central lobe not undulate and lateral lobes moderately undulate. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Violet-blue, near N92A. Lateral lobes — Green-white, near RHS 157C; petal striped violet, RHS 83A, at the base with a yellow-orange dot, near RHS 14A, also at the base. Color when opening, lower surface — Central lobe — Violet-blue, near RHS N92A, to green-white, near RHS 157B, at the base. Lateral lobes — Green-white, near RHS 157D; petal striped purple, lighter than RHS 79D, at the base. Color when fully opened, upper surface — Central lobe — Violet-blue, near RHS N92A. Lateral lobes — Purple, lighter than RHS 79D; petal striped violet, RHS 83A, at the base with a yellow-orange dot, near RHS 22A, also at the base. Color when fully opened, lower surface — Central lobe — Greyed-purple, near RHS N186B, and lighter towards the base, near RHS N187D. Lateral lobes — Greyed-purple, near RHS N187D. Fading, upper surface — Not fading. Fading, lower surface — Not fading. Venation color, fully opened, upper surface — Central lobe — Violet-blue RHS 91C. Lateral lobes — Purple, lighter than RHS 79D; violet at the base, near RHS 83A. Venation color, fully opened, lower surface — Central lobe — Greyed-purple, near RHS N186B, and lighter towards the base, near RHS N187D. Lateral lobes — Greyed-purple, near RHS N187D.

*Spurs*.—Quantity — Average of 1. Length — Approximately 1.0 cm. Diameter — Approximately 0.4 cm. Vertical height — Approximately 0.7 cm, at the base. Shape — Short triangular. Apex — Bluntly acute. Base — Broad Cuneate. Margin — Entire. Pubescence, texture and luster — Glabrous, smooth, and matte. Color — Greyed-purple, near RHS N187C.

*Sepals*.—Quantity — Average of 3 unfused sepals. Arrangement — One dorsal sepal and two lateral sepals. Length — Dorsal sepal — Approximately 5.8 cm. Lateral sepals — Approximately 5.6 cm. Width — Dorsal sepal — Approximately 4.8 cm. Lateral sepals — Approximately 5.9 cm. Shape — Both the dorsal sepal and lateral sepals are broad ovate. Apex — Obtuse. Base — Cuneate. Margin — Entire and moderately to highly undulate. Pubescence, texture and luster — Glabrous, velvety, and matte. Color when opening — Dorsal sepal, upper surface — Green-white, near 157C to 157D; tinged with greyed-purple, near RHS N187D, near the apex and violet, near RHS N87D, at the apex; sepal moderately dotted with greyed-purple RHS N187A. Dorsal sepal, lower surface — Green-white, near 157D; tinged with violet-blue, near RHS 90D and lighter, towards the apex; sepal slightly dotted with greyed-purple, RHS N187A to N187B. Lateral sepal, upper surface — Greyed-green, near RHS 195B; tinged with greyed-purple, near N187C to 187D, towards the apex; sepal moderately dotted with greyed-purple N187A; striped with violet at the base, nearest to RHS 86D. Lateral sepal, lower surface — Greyed-green, near RHS 195D; tinged with purple, near 83D, towards the apex; sepal very slightly dotted with greyed-purple RHS N187A to N187B; striped with violet at the base, nearest to RHS 86D. Color when fully opened — Dorsal sepal, upper surface — White, near 155C; tinged with violet, near RHS N88C to N88D, towards the apex; sepal densely dotted with violet RHS 83A. Dorsal sepal, lower surface — White, near 155C; tinged with violet-blue, near RHS 90D, towards the apex. Lateral sepal, upper surface — Green-white, near RHS 157C to 157D; strongly tinged with violet, near RHS 86D, towards the apex; sepal densely dotted with violet-blue RHS N92A. Lateral sepal, lower surface — Greyed-green, near RHS 195C to 195D; strongly tinged with violet, near 86D, towards the margins and apex; sepal very slightly dotted with greyed-purple RHS N187A to N187B. Fading, upper surface — Not fading. Fading, lower surface — Not fading. Venation color, fully opened, upper surface — Dorsal sepal — Violet, near RHS N87A to N87C. Lateral sepal — Violet, near RHS 86A. Venation color, fully opened, lower surface — Dorsal sepal — Violet-blue, near RHS 90D and lighter. Lateral sepal — Violet-blue, near RHS 90B to 90C.

*Pedicels*.—Length — Approximately 6.0 cm. Diameter — Approximately 0.5 cm. Angle — Approximately 70° angle to peduncle axis. Strength — Moderate. Texture — Glabrous, axially angled with 5 "ribs", axially twisted (due to resupination). Luster — Glossy. Color — White, RHS N155B; tinged with purple, near RHS 75C, towards the distal end and yellow-green, near RHS 147D and lighter, toward the proximal end.

*Bract*.—Quantity — One bract present at the base of each pedicel. Shape — Reniform; folded around the base of the pedicel. Dimensions — Average of 1.3 cm long and 1.8 cm wide. Apex — Broad acute. Base — Broad Cuneate. Margins — Entire. Color, both surfaces — Yellow-green, near RHS 144C.

Reproductive organs:

*Column*.—Length — Approximately 0.5 cm. Diameter — Approximately 0.7 cm. Color — White RHS NN155A.

*Ovary*.—Position — Inferior. Diameter — Approximately 0.2 cm. Color — Purple RHS 75D.

*Pollinia color*.—Yellow-orange RHS 14A.

Seed and fruit: No fruit and seed production has been detected to date.

COMPARISONS WITH THE PARENT PLANTS

Plants of the new cultivar 'SPCDW1404' are similar to the seed parent, *Vanda* 'RCB', in most horticultural characteristics. However 'SPCDW1404' differs from the seed parent in the following characteristics:

1. The flowers of 'SPCDW1404' exhibit a dark purple general tonality, whereas the flowers of 'RCB' exhibit a lighter purple general tonality.
2. The sepal and petal color pattern of 'SPCDW1404' exhibits more deep purple spots when compared to the sepal and petal color pattern of 'RCB'.
3. The flowers of 'SPCDW1404' are smaller than those of 'RCB'.

Plants of the new cultivar 'SPCDW1404' are similar to the pollen parent, *Vanda* 'D2N', in most horticultural characteristics. However 'SPCDW1404' differs from the pollen parent in the following characteristics:

1. The flowers of 'SPCDW1404' exhibit a dark purple general tonality, whereas the flowers of 'D2N' exhibit a red-purple general tonality.
2. The petals and sepals of 'SPCDW1404' are smaller than those of 'D2N'.
3. 'SPCDW1404' exhibits fewer flowers on each inflorescence.

COMPARISON WITH THE MOST SIMILAR *VANDA* CULTIVAR KNOWN TO THE INVENTOR

'SPCDW1404' is similar in many horticultural characteristics to the commercial variety *Vanda* 'SPCDW1310' (U.S. Plant Pat. No. 27,389). However 'SPCDW1404' differs from 'SPCDW1310' in the following characteristics:

1. The flowers of 'SPCDW1404' exhibit a dark purple general tonality, whereas the flowers of 'SPCDW1310' exhibit a lighter purple general tonality.
2. The dorsal sepal and petal margins of 'SPCDW1404' exhibit a higher degree of ruffling when compared to the dorsal sepal and petal margins of 'SPCDW1310'.
3. The spotting pattern on the dorsal sepals and petals of 'SPCDW1404' exhibits pronounced dark purple spots contrasted against a lighter background, whereas the pattern on the dorsal sepals and petals of 'SPCDW1310' exhibit less pronounced spots with blurred margins against a lighter background.
4. The flower petals of 'SPCDW1404' exhibit a higher degree of overlapping when compared to the petals of 'SPCDW1310'.

That which is claimed is:

1. A new and distinct variety of *Vanda* plant named 'SPCDW1404', substantially as described and illustrated herein.

* * * * *